United States Patent [19]

Blachford

[11] 4,316,852

[45] Feb. 23, 1982

[54] MANUFACTURE OF METALLIC SOAPS

[75] Inventor: John Blachford, Westmount, Canada

[73] Assignee: H. L. Blachford, Limited, Montreal, Canada

[21] Appl. No.: 130,080

[22] Filed: Mar. 13, 1980

[30] Foreign Application Priority Data

Mar. 29, 1979 [CA] Canada ................................. 324476

[51] Int. Cl.$^3$ ........................... C11C 1/00; C07F 7/24
[52] U.S. Cl. ................................. 260/414; 260/429 R; 260/429.9; 260/435 R; 260/439 R
[58] Field of Search ............... 260/414, 429 R, 435 R, 260/429.9, 439 R

[56] References Cited

U.S. PATENT DOCUMENTS

| | | | |
|---|---|---|---|
| 293,344 | 2/1884 | Michaud et al. | 260/414 |
| 2,211,139 | 8/1940 | Licata | 260/414 |
| 4,218,386 | 8/1980 | Logan et al. | 260/415 |

Primary Examiner—John F. Niebling

Attorney, Agent, or Firm—Bachman and LaPointe

[57] ABSTRACT

Metallic soaps, particularly zinc soaps are produced from a reaction mixture initially comprising a metal oxide or hydroxide, for example, zinc oxide, water and a glyceryl ester, particularly a triglyceride, the ester and said metal oxide or hydroxide being present in at least approximately stoichiometric amounts; the reaction mixture is agitated and the reactants are reacted in the agitated mixture to produce a metallic soap and glycerine, at a temperature at which the metallic soap is molten, in the presence of an excess of water effective to dissolve the glycerine formed in the reaction mixture such that reaction between by-product glycerine and the product metallic soap is substantially hindered, eventually the reaction mixture is allowed to separate into an aqueous layer and a molten layer of product metallic soap under a pressure such that the aqueous layer is essentially quiescent, and the molten metallic soap layer is dissociated from the aqueous layer; in this way metallic soaps of high purity can be obtained.

19 Claims, No Drawings

MANUFACTURE OF METALLIC SOAPS

BACKGROUND OF THE INVENTION

1. Field of the Invention

This invention relates to the manufacture of water-insoluble heavy metal soaps or metallic soaps and, more particularly, it relates to the manufacture of those metallic soaps which, in their molten state, are pourable liquids. It is therefore chiefly concerned with the soaps of cadmium, cobalt, lead, manganese, copper and zinc.

2. Description of the Prior Art

Metallic soaps have found wide application in industry, for example, as waterproofing agents, thickening and suspending agents, and as lubricants; they are also employed in cosmetics, lacquers, plastics, in powder metallurgy, as mold release agents, flattening agents, fillers, anti-foaming agents and driers in paints, and in tablet manufacture. They are also used as heat and light stabilizers for plastics, especially polyvinyl chloride. The most common metallic soaps are those prepared from calcium, zinc, magnesium, barium and aluminum.

The heavy metal or metallic soaps have conventionally been prepared from the metal oxides or metal salts and aliphatic carboxylic acids, particularly the higher fatty acids containing from about 12 to 22 carbon atoms, which acids are known and sold to the industry as commercial fatty acids. The commercial fatty acids as commonly used are usually mixtures of higher fatty acids in which the name attached to them may be only the dominant acid of the mixture. In some grades of commercial stearic acid, however, the dominant fatty acid is not stearic acid but another fatty acid, for example, palmitic acid.

The three basic methods conventionally employed for the manufacture of metallic soaps are described in U.S. Pat. No. 2,890,232, Russell H. Rogers, Jr. et al, issued June 9, 1959 and U.S. Pat. No. 3,803,188, Leonard Frank Scott et al, issued Apr. 9, 1974. The manufacture of metallic soaps is also described in U.S. Pat. Nos. 2,945,051, Gerald M. Davis, issued July 12, 1960 and 2,650,932, Leonard M. Kebrich et al, issued Sept. 1, 1953.

Metallic soaps of the higher fatty acids, the most common of which are the metallic stearates derived from commercial grades of stearic acid, are prepared by two principal methods:

(i) DOUBLE DECOMPOSITION PROCESS

This is the oldest process and probably still the one most commonly used. A hot aqueous solution of the sodium salt of the fatty acid is first prepared by the addition of aqueous caustic soda to a mixture of the fatty acid in hot water. The sodium salt is then reacted with a hot aqueous solution of an appropriate metal salt. The insoluble precipitate of the fatty acid metallic soap is filtered, washed free of the soluble sodium salt, dried, and ground to a fine powder. By proper control of the reaction conditions, including temperature, rate of addition of reactants, and degree of dilution, a product with a fine particle size and of high purity can be obtained. The production cost, however, is high, especially because of the filtration, washing, and drying operations required. The process also has the drawback that frequently it creates a water pollution problem. Zinc stearate is manufactured commercially employing this process by the action of sodium stearate on a solution of zinc sulphate.

(ii) REACTION OF METALS, METAL OXIDES OR METAL HYDROXIDES WITH MOLTEN FATTY ACIDS

(a) Fusion Process

Only certain metallic soaps can be formed by this method. The metallic soap is formed by reacting the molten fatty acid with the appropriate metal oxide or hydroxide at a temperature above the melting point of the metallic soap to be formed, and generally at a temperature considerably above this, because, during the reaction, water is formed and this must be driven off. Generally, the reaction requires in the neighbourhood of 5 hours for completion. This process can only be used for making metallic soaps which are pourable in their molten state. It, therefore, cannot be used for such metallic soaps as calcium or barium stearate, but it is suitable for zinc and lead stearates. The final product is in the form of flakes or lumps and a considerable energy must be expended in grinding it to the required very fine particle size. This process does have the advantage of not requiring the use of caustic soda, and no filtering or drying is required. It also does not lead to any water pollution or the consumption of any water.

(b) Modified Fusion Process

This is much like the fusion process (a), except that a small amount of water is added to the mixture of molten fatty acid and metal oxide or hydroxide. The water acts as a catalyst and allows the reaction to be carried out at a somewhat lower temperature, and more quickly. The final product produced is very much like, if not identical to, that resulting from the fusion process (a).

(c) Fusion in an Aqueous Slurry

In this process, the molten fatty acid is first emulsified in water using an appropriate emulsifying agent. To this aqueous emulsion, is added an aqueous slurry of the metal oxide or hydroxide. The metallic oxide or hydroxide reacts with the fatty acid to form the metallic soap. This is then removed by filtration, during which it is washed, and then it is dried and ground. The product is considerably easier to grind because it is produced in the form of coarse particles. These particles, however, are much coarser than those produced in the double decomposition process.

(d) Miscellaneous Fusion Methods

Occasionally, it is possible and of commercial value to react certain metals directly with molten fatty acid. For example, iron stearate may be prepared by this method; however, hydrogen rather than water is actually a by-product of reaction and, because the reaction generally has to be carried out at an unusually high temperature, the colour of the resulting metallic soap is poor.

SUMMARY OF THE INVENTION

The present invention provides a new and improved method for the manufacture of metallic soaps that are pourable in their molten state, utilizing oxides or hydroxides of divalent metals and appropriate fats or oils rather than the fatty acids derived from such fats and oils.

The method of the invention permits the production of metallic soaps in good yield and purity with low free fatty acid content.

According to the invention there is provided a process for producing a metallic soap having a viscosity such that it is a pourable liquid when molten, of a monocarboxylic acid of the formula R-COOH wherein R is a linear or branched, saturated or unsaturated, unsubstituted or substituted by one or more hydroxy groups, aliphatic hydrocarbon radical of 5 to 21 carbon atoms, which comprises: (i) forming a reaction mixture initially comprising a metal component comprising a metal oxide selected from the group consisting of oxides of cadmium, lead and zinc or a metal hydroxide selected from the group consisting of hydroxides of cobalt, manganese, and zinc, water and a glyceryl ester of formula (I):

$$H_2C(OR_1)CH(OR_2)CH_2(OR_3) \qquad (I)$$

wherein $R_1$, $R_2$ and $R_3$, which may be the same or different are selected from the group consisting of hydrogen and linear or branched, unsubstituted or substituted by one or more hydroxyl groups, saturated or unsaturated aliphatic hydrocarbon acyl radicals of 6 to 22 carbon atoms, provided that at least one of $R_1$, $R_2$ and $R_3$ is an acyl radical, said ester and said metal oxide or hydroxide being present in at least approximately stoichiometric amounts; (ii) agitating said reaction mixture; (iii) reacting the reactants in the agitated mixture to produce a metallic soap of the carboxylic acid and glycerine, at a temperature at which the metallic soap is molten, in the presence of an excess of water effective to dissolve the glycerine formed in the reaction mixture such that reaction between the reactants proceeds in favour of metallic soap production and the reaction between glycerine and the product metallic soap is substantially hindered; (iv) continuing the reacting in (iii) until substantially no more metallic soap is formed; (v) allowing the reaction mixture to separate into an aqueous layer and a molten layer of product metallic soap substantially free of metallic oxide or metallic hydroxide, carboxylic acid and glyceryl ester, under a pressure such that said aqueous layer is essentially quiescent, and (vi) dissociating the molten metallic soap layer from the aqueous layer.

DESCRIPTION OF THE PREFERRED EMBODIMENTS

The method of the invention employs a reaction between a metal oxide or hydroxide, a glyceryl ester, particularly a mono-, di or triglyceride, preferably a triglyceride, for example, unhydrogenated or hydrogenated, naturally occurring, vegetable oil or animal fat, and, in the case of the oxide, water. A particular advantage of the method of the invention, which employs a glyceryl ester, particularly a triglyceride, instead of a fatty acid or mixture of fatty acids derived from the corresponding triglyceride, is that it is unnecessary to carry out the procedure of first deriving the acid or acids from the corresponding glyceryl ester prior to forming the metallic soap by reacting the metal oxide or hydroxide with the fatty acid; instead, the metallic soaps are formed directly from the glyceryl esters. Furthermore, unlike the double decomposition process, no caustic soda is required, and it is not necessary to carry out any filtering, washing or drying.

In one embodiment of the process of the invention an oxide of a heavy metal, particularly a divalent metal, is reacted with the glyceryl ester of formula (I), which may be a mono-, di- or triglyceride, and water, with elimination of glycerine. The reaction proceeds in accordance with equation (I)—

$$pH_2C(OR_1)CH(OR_2)CH_2(OR_3) + qMO(\text{or } M(OH)_2) + qH_2O \rightarrow pCH_2OH.CH(OH).CH_2OH + qR_4OMOR_5$$

wherein $R_1$, $R_2$ and $R_3$ are as defined above in formula (I), M is the metal, $R_4$ and $R_5$, which may be the same or different, are acyl radicals selected from $R_1$, $R_2$ and $R_3$, p is an integer of 1 or 2 and q is an integer of 1 or 3. When the glyceryl ester is a monoglyceride, p is 2 and q is 1; when the glyceryl ester is a diglyceride, p and q are both 1; and when the glyceryl ester is a triglyceride, p is 2 and q is 3.

In another embodiment a heavy metal hydroxide is employed in place of the oxide and no water is required in the chemical reaction with the glyceryl ester although water is still required in the reaction mixture to dissolve the glycerine; the values for p and q are as indicated in equation (I) except that for the water as reactant q is o.

The heavy metal of the metal oxide may be cadmium, lead or zinc; the heavy metal of the metal hydroxide may be cobalt, manganese, copper or zinc. The preferred metal oxide is zinc oxide; the preferred metal hydroxide is cobaltous hydroxide. Although oxides and hydroxides of some of the alkaline earth and other heavy metals will react with glyceryl esters, the resulting metallic soaps do not form pourable liquids when heated above their melting points and, consequently, the separation of the resulting metallic soaps from the solution of by-product glycerine and water is difficult and not commercially practical. The present invention is concerned only with those metallic soaps which are pourable liquids at temperatures exceeding their melting points. For the purposes of this invention, a pourable liquid is defined as one having a viscosity of less than 1,000,000 and preferably less than 500,000 cps.

In a preferred embodiment of the process of this invention, the glyceryl ester is a triglyceride selected from the triglycerides which are derived from, or contained in, animal or vegetable fats or oils, since these are more readily available commercially. Such triglycerides include those in which the aliphatic hydrocarbon radical is saturated or unsaturated.

Triglycerides in which one or more of $R_1$, $R_2$ and $R_3$ has less than 6 carbon atoms or more than 22 carbon atoms will produce metallic soaps by the process of the invention, however, such triglycerides are rare and not generally commercially available.

A large number of triglycerides, which are derived from or contained in animal or vegetable fats or oils, may be used in the invention. The degree of unsaturation of a triglyceride is indicated by the iodine value. The higher the iodine value, the higher the degree of unsaturation. Frequently, it is desirable to reduce the degree of unsaturation of a triglyceride and this can be accomplished by reacting the triglyceride with hydrogen, the process being called hydrogenation. The degree to which the unsaturation is reduced is determined by the amount of hydrogen which is allowed to react with the triglyceride.

Occasionally, complete saturation or hydrogenation is desired and, in this case, the iodine value is reduced to essentially zero. In other instances, it may be sufficient to merely reduce the iodine value from, say, 40 to 15.

The triglycerides which occur naturally differ widely in iodine value and also in composition. This is demonstrated in Table I below.

colour of the metallic soap produced is whiter and the colour stability on heating is greater.

The melting point of the metallic soap depends on the degree of unsaturation in the aliphatic hydrocarbon radicals, or in other words it depends on the iodine

TABLE I

APPROXIMATE COMPOSITION OF VARIOUS UNHYDROGENATED FATS AND OILS

| Unhydro-genated Fat or Oil | Iodine Value | APPROX. NATURE AND AMOUNTS (IN WT. %) OF DERIVABLE SATURATED FATTY ACIDS | | | | | | APPROX. NATURE AND AMOUNTS (IN WT. %) OF DERIVABLE UNSATURATED FATTY ACIDS | | | | |
|---|---|---|---|---|---|---|---|---|---|---|---|---|
| | | caprylic | capric | lauric | myristic | palmitic | stearic | oleic | erucic | ricino-leic | lino-leic | lino-lenic |
| Castor | 85 | — | — | — | — | — | 0.3 | 8.2 | — | 87.6 | 3.6 | — |
| Coconut | 10 | 8.0 | 7.0 | 48.2 | 17.3 | 8.8 | 2.0 | 6.0 | — | — | 2.5 | — |
| Cotton-seed | 110 | — | — | — | 0.5 | 22.9 | 2.2 | 24.7 | — | — | 49.7 | — |
| Lard | 55 | — | — | — | 1.0 | 26.0 | 11.0 | 48.7 | — | — | 12.2 | 0.7 |
| Linseed | 180 | — | — | — | — | 6.4 | 4.5 | 21.0 | — | — | 17.4 | 50.6 |
| Palm | 50 | — | — | — | 1.0 | 42.5 | 4.0 | 43.0 | — | — | 9.5 | — |
| Peanut | 90 | — | — | — | — | 7.0 | 5.0 | 60.0 | — | — | 21.0 | — |
| Rape-seed | 100 | — | — | — | 1.0 | 1.0 | 1.0 | 29.0 | 50.0 | — | 15.0 | 1.0 |
| Soya-bean | 135 | — | — | — | — | 6.5 | 4.2 | 28.0 | — | — | 52.6 | 8.0 |
| Beef Tallow | 40 | — | — | — | 2.2 | 35.0 | 15.7 | 44.4 | — | — | 2.2 | 0.4 |

During hydrogenation, the double bonds in the unsaturated aliphatic hydrocarbon radicals of the triglyceride molecules are gradually replaced with single bonds and, in this way, the chemical composition is significantly changed. For example, when the unsaturated hydrocarbon radical of oleic acid radical is hydrogenated, the oleic acid is converted to stearic acid. The typical composition of the naturally occurring triglycerides of Table I after hydrogenation is shown in Table II below.

value of the triglyceride employed. The lower the iodine value, i.e., the higher the saturation of the aliphatic hydrocarbon radicals, the higher the melting point of the metallic salt. For a given chain length or number of carbon atoms in a fatty acid aliphatic hydrocarbon radical, the greater the number of carbon-carbon double bonds in the chain, the lower will be the melting point; for example zinc stearate melts at 120° C. and zinc oleate melts at 70° C.

In carrying out the process of the invention on a

TABLE II

APPROXIMATE COMPOSITION OF VARIOUS HYDROGENATED FATS AND OILS

| Hydro-genated Fat or Oil | Iodine Value | APPROX. NATURE AND AMOUNTS (IN WT. %) OF DERIVABLE SATURATED FATTY ACIDS | | | | | | | APPROX. NATURE AND AMOUNTS (IN WT. %) OF DERIVABLE UNSATURATED FATTY ACIDS | |
|---|---|---|---|---|---|---|---|---|---|---|
| | | caprylic | capric | lauric | myristic | palmitic | stearic | 12-hydroxy-stearic | other | oleic |
| Castor | 2 | — | — | — | — | 2 | 10 | 88 | | — |
| Coconut | 1 | 4 | 6 | 49 | 21 | 10 | 10 | — | | — |
| Cotton-seed | 5 | — | — | — | 1 | 23 | 70 | — | | 6 |
| Lard | 3 | — | — | — | 1 | 26 | 69 | — | | 4 |
| Linseed | 2 | — | — | — | — | 6 | 92 | — | | 2 |
| Palm | 1 | — | — | — | 1 | 43 | 55 | — | | 1 |
| Peanut | 4 | — | — | — | — | 7 | 81 | — | | 5 |
| Rape-seed | 6 | — | — | — | 1 | 1 | 39 | — | 51 Behenic | 7 |
| Soya-bean | 7 | — | — | — | — | 7 | 85 | — | | 8 |
| Beef Tallow | 2 | — | — | — | 3 | 28 | 65 | — | | 2 |

It is especially preferred to employ a triglyceride having an iodine value of less than 50, and preferably less than 10. Some of the naturally occurring triglycerides have an iodine value of this order, but others must be hydrogenated to convert them into triglycerides having a low iodine value. The advantage in employing triglycerides having a lower iodine value is that the commercial scale, commercially available materials are utilized. It will be appreciated that commercially available materials are of varying grades of composition.

In the specification, identification of materials by the chemical name is intended to embrace both the chemically pure material and the commercially available product. For example, the "zinc stearate" produced in the examples illustrating this invention will be a commercial grade of zinc stearate, similar to the product derived commercially by reacting zinc oxide with "stearic acid", which term covers such products as single-pressed, double-pressed and triple-pressed stearic acid and also mixtures of fatty acids derived from the complete or incomplete hydrogenation and subsequent hydrolysis of certain animal and vegetable fats and oils, for example, tallow fat and soybean oil.

The triglycerides employed in the invention have mixtures of aliphatic hydrocarbon radicals similar to those in the fatty acids derived from them, so that the composition of the metallic soaps produced in this invention from a particular fat or oil will be similar to that produced by the conventional method from a mixture of fatty acids derived from that fat or oil.

Thus it will be recognized that the nature of the commercially available reactants employed in the invention results in metallic soap products which, essentially, are mixtures of different metallic soaps rather than a single metallic soap. Of course, the process of the invention can be utilized to produce particular metallic soaps which are not mixtures by appropriate selection of triglycerides in which all the aliphatic hydrocarbon radicals are the same, but for most purposes such selection is unnecessary as the different metallic soaps in a metallic soap product have sufficiently similar properties and characteristics for most industrial uses.

As illustrative of the novel process of the invention, zinc stearate can be prepared by heating together under conditions of agitation in an enclosed reactor (for example, an autoclave) zinc oxide, hydrogenated tallow, and water according to the following equation (II):

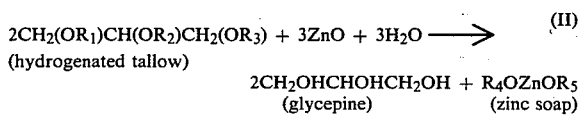

where $R_1$, $R_2$ and $R_3$ are acyl radicals as defined previously and are the same or different for each molecule of hydrogenated tallow, and are present in amounts corresponding approximately to the composition given in Table I, and $R_4$ and $R_5$, which may be the same or different, are acyl radicals selected from $R_1$, $R_2$ and $R_3$.

When the reaction is complete, the agitation is stopped and the temperature is maintained above the melting point of the product zinc soap. In a preferred embodiment the pressure is increased by the introduction of an inert gas, for example, air or nitrogen, so that the pressure is substantially above the vapour pressure of the aqueous glycerine at the temperature in the autoclave. Under these conditions of temperature and pressure and in the absence of agitation, the molten zinc soap forms a discrete layer above an aqueous layer of glycerine. Having obtained this layer separation, it is a simple matter to drain off the lower aqueous layer before draining off the molten zinc soap into a separate container.

It is an important aspect of this invention that the reaction conditions be such that a thorough separation of the metallic soap from the aqueous glycerine is achieved. Table III below shows the dependence of specific gravity on temperature for several metallic soaps and on both temperature and glycerine content for several different solutions of glycerine in water. These results show that when certain metallic soaps are in the presence of certain glycerine in water solutions at a particular temperature, the specific gravity of the molten metallic soap and that of the aqueous glycerine solution are equal and it is therefore impossible to achieve the formation of the two distinct layers of immiscible materials. If the specific gravity of the molten metallic soap is only slightly less or slightly greater than that of the aqueous solution, it is very difficult, and frequently impossible, to obtain a complete separation.

It is therefore appropriate to control the process conditions such that there is an adequate difference in the specific gravities of the molten metallic soap and the aqueous glycerine to permit complete separation to form distinct layers. The specific gravities may suitably be altered by varying the temperature or by diluting the reaction mixture with further quantities of water.

TABLE III

| SPECIFIC GRAVITY FOR VARIOUS METALLIC SOAPS AND FOR VARIOUS AQUEOUS GLYCERINE SOLUTIONS | | | | | | | |
|---|---|---|---|---|---|---|---|
| | TEMPERATURE IN °C. | | | | | | |
| MATERIAL | 20 | 50 | 100 | 130 | 150 | 185 | 200 |
| 10% glycerine in water | 1.025 | 1.012 | 0.983 | 0.960 | 0.943 | 0.908 | 0.891 |
| 20% glycerine in water | 1.051 | 1.038 | 1.008 | 0.986 | 0.969 | 0.934 | 0.918 |
| 30% glycerine in water | 1.077 | 1.063 | 1.033 | 1.011 | 0.994 | 0.961 | 0.945 |
| 40% glycerine in water | 1.104 | 1.089 | 1.058 | 1.036 | 1.019 | 0.987 | 0.972 |
| cadmium stearate | 1.21 | | | 1.00 | 0.99 | 0.95 | |
| copper stearate | 1.10 | | | | | | |
| cobalt stearate | 1.13 | | | | | | |
| lead stearate | 1.37 | | | 1.17 | 1.15 | 1.11 | |
| manganese stearate | 1.22 | | | | | | |
| zinc stearate | 1.09 | | | | 0.92 | 0.91 | 0.89 |
| zinc palmitate | 1.12 | | | | | | |

An important feature of the invention is that during the process step leading to the separation of the two layers, one layer composed of molten metallic soap and the other of an aqueous solution of glycerine, the pressure in the reactor should exceed the vapour pressure of the aqueous solution of glycerine at the temperature within the reactor; otherwise the aqueous solution will continue to boil and this boiling action will effect an agitation that will make it impossible to achieve a complete separation of the metallic soap from the glycerine in water solution. At this stage of the process the pressure is controlled so that the solution forms an essentially quiescent layer.

If the reactor is air-tight and the air initially present in the reactor is not expelled then the pressure will remain above the vapour pressure of the aqueous glycerine solution at all times during the course of the reaction and, therefore, it will be possible to obtain a phase separation once the reaction has been completed and the agitation stopped since a quiescent aqueous layer will then form. However, as soon as the removal of one of the phases from the reactor is begun, for example, by draining or decanting, the pressure in the reactor will decrease, and, when it equals the vapour pressure of the aqueous solution in the reactor, boiling will commence, resulting in the mixing of the two phases or layers. In order to achieve the removal of one or the other layer from the reactor without disrupting the quiescent state, an inert gas is suitably introduced so that the pressure in the reactor is such that it always exceeds the vapour pressure of the aqueous solution as long as the two phases are present in the reactor following the reaction. Of course, other means of ensuring an adequate pressure in the reactor can also be employed, such as maintaining a very high pressure in the reactor throughout the process so that during removal of one of the layers from the reactor, the pressure does not fall as low as the vapour pressure of the aqueous solution.

If the metallic soap melts considerably below 100° C. and is a pourable liquid below this temperature, the reaction can be carried out at a temperature below 100° C., and the separation of the molten metallic soap from the glycerine in water solution can be obtained at atmospheric pressure. However, very few metallic soaps of commercial value have melting points below 100° C. and, furthermore, the rate of reaction at temperatures below about 100° C. is impractically slow.

The molten metallic soap may form the upper or lower layer in the reactor depending on the relative specific gravities of the metallic soap and the aqueous glycerine layer at the temperature in the reactor, shown in Table III above.

The relative amounts of the three components in the reaction mixture is important. An excess of the metal oxide or hydroxide above the stoichiometric amount required to completely react with the triglyceride will lead to contamination of the metallic soap with the metal oxide or hydroxide. If the amount of metal oxide or hydroxide is below that required stoichiometrically, the product metallic soap will be contaminated with unreacted triglyceride and possibly some free fatty acid.

The amount of water required is particularly important; but, in this instance, the amount by weight must be considerably greater than the amount by weight of glycerine produced. This is because the reaction between the glyceride, metal oxide and water or glyceride and metal hydroxide is a reversible reaction and, if only the stoichiometric amount of water is used, the reaction does not proceed nearly to completion. In order to promote the metallic soap-producing reaction over the reverse reaction it is necessary to employ a large excess of water to dissolve the by-product glycerine. If insufficient water is available, part of the glycerine will dissolve in the metallic soap and some of this glycerine will react with the metallic soap to produce metal oxide, triglyceride, a certain amount of mono- and di-glyceride and some water. On the other hand, it is wasteful to use more water than is necessary and, in addition, the use of a great excess of water leads to a lower yield of metallic soap for a given vessel size.

Even when the amount of water used is equal to the amount of glycerine produced the metallic soap that is separated after the reaction contains over 3% of glycerides. When the amount of water is reduced even further, so that no excess over the stoichiometric amount is present, the reaction goes only to about 80% of completion, as indicated by the presence of approximately 20%, by weight, of glycerides in the metallic soap. In both instances, there is also a substantial amount of glycerine dissolved in the soap. A product of sufficient purity for commercial applications can be obtained if the amount of water corresponds to about 4 times the stoichiometric amount of glycerine produced on completion of the reaction. It is well known that many metallic soaps are readily hydrolyzed, at elevated temperatures, to metallic oxide and fatty acid. It is therefore surprising that, considering the large amount of water present in the process, an insignificant amount of hydrolysis occurs. Generally, it is appropriate to have a content of water in the reaction mixture at least equal to, preferably about 2 to about 10, more preferably about 2 to about 7, and most preferably about 3 to 5 times the stoichiometric amount of glycerine produced on completion of the reaction.

In another respect, the amount of water employed is important, because, as previously discussed, it affects the specific gravity of the solution of glycerine in water. This specific gravity must be significantly different from that of the molten metallic soap if a substantially complete separation of the molten metallic soap from the glycerine in water solution to produce layers, is to be achieved.

The presence of only a small amount of glycerine in the product metallic soap is deleterious because, at elevated temperatures, the glycerine reacts with the metallic soap to produce water, metal oxide and glycerides. However, it is very difficult, and perhaps impossible, to completely eliminate the presence of trace amounts of glycerine in the soap.

The reaction temperature should exceed the melting point of the metallic soap to be formed; otherwise, the reaction will not go nearly to completion. The higher the temperature, the faster the reaction occurs and the reaction rate increases by approximately 50% for every 10° C. increase in reaction temperature. On the other hand, high temperatures, such as those well in excess of 200° C., should be avoided because they frequently cause discolouration of the metallic soap. Furthermore, high temperatures lead to build-up of high pressures in the reactor which in turn necessitate the use of otherwise unnecessary expensive production equipment.

In the case where zinc stearate is being manufactured, it has been found that at a reaction temperature of 130° C., the time required to complete the reaction is approximately 6 hours and, at a temperature of 220° C., this time is reduced to less than 1 hour. If the reaction is carried out for too short a time, the reaction will be incomplete. However, if it is carried out for an excessively long time, discolouration may occur.

The best reaction temperature is therefore one that is as high as possible, but with the practical upper limit being about 250° C. because of the possibility of thermal decomposition. Further, as indicated above high reaction temperatures result in the build up of high pressures. Water vapour pressure increases rapidly with temperature: at 150° C., the vapour pressure is 54 psig (pounds per square inch gauge); at 175° C., it is 115 psig.; at 185° C., it is 148 psig.; at 200° C., it is 211 psig.; at 220° C., it is 322 psig. and at 250° C., it is 562 psig.; clearly, therefore, the practical reaction temperature will be partly determined by the ability of the reaction vessel employed to withstand the high pressures associated with high reaction temperature.

A reaction temperature of about 100° C. to about 250° C., preferably about 125° C. to 200° C. and most preferably about 175° C. to 195° C., and a reaction time of 0.5 to 10 hours, preferably about 2 to 5 hours, are found suitable for most purposes, in order to obtain a satisfactory rate of reaction while avoiding discolouration of the product metallic soaps by prolonged exposure to elevated temperatures.

In addition to the temperature, the reaction time is somewhat dependent on the degree of agitation. Over a fairly broad range, the reaction time decreases as the degree of agitation increases. Above a certain level of agitation the reaction time is not affected and, below a certain level of agitation, the reaction will take an extremely long time to go to completion. The agitation causes the molten glyceryl ester, for example, triglyceride, to disperse as droplets in the water and the more vigourous the agitation, the smaller the droplet size. This smaller droplet size results in a greater area of interfacial contact between the water, the metallic oxide and the glyceryl ester, and hence a faster reaction.

At the commencement of the reaction, agitation is more important with regard to forming small droplets of the molten glyceryl ester in water, particularly when the ester is a triglyceride. Once the reaction has begun, mono- and diglycerides are formed from the triglyceride and these act as emulsifying agents, which greatly reduce the need for strong agitation.

A particularly important reason for having strong agitation is to keep the metal oxides and hydroxides suspended and prevent them from settling to the bottom of the reaction vessel where they cannot react. Many of the metal oxides and hydroxides are very dense, especially relative to the density of water and glyceryl ester, for example, the specific gravity of zinc oxide is 5.7, that of lead oxide is 9.6, and that of cadmium oxide is 8.2.

In addition to the specific gravity, the other important property governing the extent to which a dispersed solid tends to settle is the particle size. The larger the particle size, the greater the agitation must be.

Thus the required agitation depends on a number of factors.

Generally it is desirable to effect an agitation that will produce a small droplet size of the glyceryl ester in water, typically of 1 micron to 5,000 microns and preferably of 1 micron to 1,000 microns.

When the glyceryl ester is a triglyceride, some of the triglyceride is converted, during the reaction, into di- and mono-glyceride. However, these are intermediates and by the time the reaction is complete, they have been completely converted into glycerine. These mono- and di-glycerides, however, are somewhat helpful, as indicated above, because they act as emulsifying agents for the triglyceride and facilitate the dispersion of the triglyceride in the water as small droplets. Certain emulsifying agents in addition to those formed in situ during the reaction may be added if it is desired to increase the rate of reaction, or for other beneficial reasons, and provided they do not interfere with the phase separation and do not significantly adulterate the metallic soap.

Because the reaction is carried out in an enclosed reactor vessel, the pressure increases as the temperature increases. This pressure may be made even higher than that corresponding to the vapour pressure of water at the reaction temperature if nitrogen, air, or some other inert gas is introduced into the reactor vessel at a pressure greater than the vapour pressure of water at the reaction temperature. As previously stated, this creation of a higher pressure is necessary after the reaction has been completed and when it is desired to separate the molten metallic soap from the solution of glycerine and water. However, the creation of such a higher pressure during the course of the reaction does not generally affect the rate of the reaction. It is unnecessary to create a high pressure during the course of the reaction, and it may be inadvisable to do so. This is because when no such additional pressure is introduced, the water in the reactor vessel boils and this boiling action serves to create a large amount of agitation, and thereby supplements the action of the mechanical agitation. The greater the total degree of agitation, the faster the reaction will occur. On the other hand, the water will not boil if the pressure in the reactor vessel exceeds the vapour pressure of the water.

The reaction rate is also dependent upon the particle size of the metal oxide or hydroxide. The finer the particle size, the faster the reaction proceeds. Preferably, the particle size should be finer than 200 mesh (ASTM) and, most preferably, it should be finer than 325 mesh. Generally the metal oxides and hydroxides have an average particle size such that at least 95% pass through a 200 mesh; the average particle size will typically be 0.3 microns to 75 microns, and preferably smaller than 45 microns.

In general the present invention provides a process which proceeds to at least 95% completion in favour of formation of metallic soap, in which the content of free acid in the soap is typically less than 1% by weight.

As indicated above the reaction proceeds via the formation of several intermediate compounds. When the reactants comprise a metal oxide, a triglyceride and water, only one or two fatty acid radicals may be removed initially from a particular triglyceride molecule to form the metallic soap. When only one is removed, the intermediate formed is a diglyceride, and when two, it is a monoglyceride. Both diglycerides and monoglycerides will, in turn, react with the metal oxide to form the metallic soap product. The diglyceride may first be converted into a monoglyceride. This also applies when a metal hydroxide, rather than an oxide, is employed.

Thus the invention embraces the process of manufacturing metallic soaps by reacting a metal oxide or hydroxide with a diglyceride or monoglyceride in water. These two glycerides are, however, generally derived from a triglyceride by reacting glycerine with triglyceride.

In order to obtain a metallic soap free of contaminating materials it is desirable to exclude additives in the reaction mixture. As indicated above the mono- and di-glycerides, which may be formed as intermediates, will function as emulsifiers to disperse the triglyceride as small droplets in the water, and their in situ formation represents an advantageous aspect of the invention. Additives that might promote the reaction, such as hydrolysis accelerators or catalysts, for example, clay, should be avoided since they would contaminate the product metallic soap.

EXAMPLES

The invention is illustrated with reference to the following examples which represent preferred procedures and embodiments, and are intended merely for purposes of illustration and are not intended to be construed as limiting the scope of the invention.

EXAMPLE 1—ZINC STEARATE FROM HYDROGENATED TALLOW, ZINC OXIDE AND WATER 800 grams of hydrogenated tallow (available under the trademark Hyfac 2120 from Emery Industries Inc.; this is a triglyceride having an iodine value of less than 1.5 and composed of esters of glycerine and a mixture of fatty acids having approximately the following composition: myristic, 3%; pentadecanoic, 1%; palmitic, 28%; margaric, 1%; stearic, 65%; and oleic, 2%) were mixed with 118.8 grams of zinc oxide having an average particle size of 0.4 $\mu$m (available under the trademark Zochem 100 from Zochem Limited) and 400 grams of water in a high pressure air-tight reactor. After 30 minutes of heating and mixing with the exhaust valve closed, the temperature had reached the desired level of 185° C. and the pressure was 150 psig. The temperature was maintained at 185° C., the pressure at 150 psig. and the agitator speed at 500 rpm. for 3 hours. After this time, it was judged that the reaction was complete. The agitator was stopped and to prevent the water from boiling, the pressure was increased from 150 psig. to 175 psig. by introducing nitrogen. After 1 hour under these static conditions, phase separation had occurred resulting in a molten layer of zinc soap on top of a solution of glycerine in water. The aqueous layer was removed through the bottom valve, and then the molten zinc soap was removed through the same valve. The separated zinc soap had a melting point of 121°–123° C., a moisture content of 0.58%, a free fatty acid content of 0.38% and on ignition produced an ash of 13.72%. The infrared spectrum showed only very weak hydroxyl and glyceride absorptions.

EXAMPLE 2—LEAD STEARATE FROM HYDROGENATED TALLOW, LITHARGE AND WATER

The procedure described in Example 1 was repeated with the zinc oxide replaced by 344.1 g. of litharge having an average particle size of 4 microns (from NL Industries Inc.). The molten lead stearate produced formed the bottom layer upon phase separation. It had a melting point of 104°–106° C. moisture content of 2.0%, ash of 28.9%, and negligible fatty acid content. The infrared spectrum showed negligible glyceride content.

EXAMPLE 3—ZINC TALLOWATE FROM TALLOW, ZINC OXIDE AND WATER

The procedure of Example 1 was followed but using unhydrogenated tallow instead of hydrogenated tallow. As in the case of zinc stearate, the molten soap formed the top layer on phase separation. It had a melting point of 89°–97° C., moisture content of 0.5%, ash of 13.8%, and free fatty acid content of 0.9%. The infrared spectrum showed negligible glyceride content.

EXAMPLE 4—ZINC COCONATE FROM COCONUT OIL, ZINC OXIDE AND WATER

The procedure of Example 1 was followed using 600 grams of refined coconut oil (from Emery Industries Inc.), 300 grams of water, and 117.9 grams of zinc oxide having an average particle size of 0.4 $\mu$m. The zinc soap produced formed the upper layer on phase separation and had the following properties: melting point, 111°–117° C.; moisture, 2.4%; ash, 17.3%; free fatty acid, 0.7%. The infrared spectrum showed negligible glyceride content.

EXAMPLE 5—CADMIUM STEARATE FROM HYDROGENATED TALLOW, CADMIUM OXIDE AND WATER

The procedure of Example 1 was followed using 800 grams hydrogenated tallow, 400 grams water and 181.1 grams cadmium oxide having an average particle size of 1 micron. However, phase separation did not occur. This was because the specific gravity of the cadmium stearate was very close to that of the aqueous solution of glycerine. On adding an additional 400 grams of water, phase separation did occur. The stearate phase formed a layer below the aqueous phase. The extra water had reduced the specific gravity of the aqueous phase to such an extent that phase separation could occur. The cadmium stearate produced had a melting point of 103°–105° C., ash of 18.1% and negligible free fatty acid and glyceride content.

EXAMPLE 6—ZINC SOAP FROM HYDROGENATED CASTOR OIL, ZINC OXIDE, AND WATER

The procedure of Example 1 was followed using 600 grams of hydrogenated castor oil, 300 grams of water, and 79.9 grams of zinc oxide, having an average particle size of 0.4 $\mu$m. The soap produced (mainly zinc 12-hydroxystearate) had the following properties: melting point 138° C., moisture 1.8%, ash 12.5%, free fatty acid 1%.

EXAMPLE 7—COBALT STEARATE FROM HYDROGENATED TALLOW, COBALT HYDROXIDE, AND WATER

The procedure of Example 1 was followed using 600 grams of hydrogenated tallow, 300 grams of water, and 97 grams of cobalt hydroxide (average particle size 1 $\mu$m). The cobalt stearate produced had the following properties: melting point 83° C., moisture 2.1%, ash 12.0%, free fatty acid 0.9%.

The percentages in the foregoing examples are by weight, unless otherwise indicated.

I claim:

1. A process for producing a metallic soap having a viscosity such that it is a pourable liquid when molten, of a monocarboxylic acid of the formula R-COOH wherein R is a linear or branched, unsubstituted or substituted by one or more hydroxyl groups, saturated or unsaturated aliphatic hydrocarbon radical of 5 to 21 carbon atoms, which comprises:

(i) forming a reaction mixture initially comprising a metal component comprising a metal oxide selected from the group consisting of oxides of cadmium, lead and zinc or a metal hydroxide selected from the group consisting of hydroxides of cobalt, manganese, and zinc, water and a glyceryl ester of formula (I):

$$H_2C(OR_1)CH(OR_2)CH_2(OR_3) \qquad (I)$$

wherein $R_1$, $R_2$ and $R_3$, which may be the same or different, are selected from the group consisting of hydrogen and linear or branched, unsubstituted or substituted by one or more hydroxyl groups, saturated or unsaturated aliphatic hydrocarbon acyl radicals of 6 to 22 carbon atoms, provided that at least one of $R_1$, $R_2$ and $R_3$ is an acyl radical, said ester and said metal oxide or hydroxide being present in at least approximately stoichiometric amounts, (ii) agitating said reaction mixture, (iii) reacting the reactants in the agitated mixture to produce a metallic soap and glycerine, at a temperature at which the metallic soap is molten, in the presence of an excess of water effective to dissolve the glycerine formed in the reaction mixture such that reaction between by-product glycerine and the product metallic soap is substantially hindered, (iv) continuing said reacting in (iii) until substantially no more metallic soap is formed, (v) allowing the reaction mixture to separate into an aqueous layer and a molten layer of product metallic soap substantially free of metallic oxide or metallic hydroxide, carboxylic acid and glyceryl ester, under a pressure such that said aqueous layer is essentially quiescent, and (vi) dissociating the molten metallic soap layer from the aqueous layer.

2. A process according to claim 1, wherein said metal component is selected from the group consisting of cadmium oxide, lead oxide and zinc oxide.

3. A process according to claim 2, wherein said glyceryl ester is a mono- or diglyceride.

4. A process according to claim 1, wherein said glyceryl ester is a triglyceride.

5. A process according to claim 2, wherein said glyceryl ester is a triglyceride.

6. A process according to claim 1, wherein said metal component is zinc oxide and the glyceryl ester is a triglyceride.

7. A process according to claim 6, wherein the triglyceride is prepared by hydrogenating a naturally occurring triglyceride.

8. A process according to claim 1, wherein said reaction in (iii) is continued for 0.5 to 10 hours.

9. A process according to claim 1, in which said reaction mixture contains at least as much water by weight as the amount by weight of glycerine that would be produced in reacting to completion.

10. A process according to claim 2, wherein said glyceryl ester comprises a mixture of at least two esters selected from the group consisting of monoglycerides, diglycerides and triglycerides of formula (I).

11. A process for producing a zinc soap having a viscosity of less than 500,000 centipoise when molten, which comprises:

(i) forming a reaction mixture initially comprising zinc oxide, water and a triglyceride in which the molar ratio of the triglyceride to the zinc oxide is about 2:3, (ii) agitating said reaction mixture, (iii) reacting the reactants in the agitated mixture to produce a zinc soap and glycerine, at a temperature at which the metallic soap is molten, in accordance with the equation (II):

$$2H_2C(OR_1)CH(OR_2)CH_2(OR_3) + 3ZnO + 3H_2O \rightarrow 2CH_2OHCHOHCH_2OH + 3R_4OZnOR_5 \quad (II)$$

wherein $R_1$, $R_2$ and $R_3$, which may be the same or different, are selected from the group consisting of linear or branched, unsubstituted or substituted by one or more hydroxyl groups, saturated or unsaturated, aliphatic hydrocarbon acyl radicals of 6 to 22 carbon atoms and $R_4$ and $R_5$, which may be the same or different, are acyl radicals selected from $R_1$, $R_2$ and $R_3$, in the presence of an excess of water effective to dissolve the glycerine formed in the reaction mixture such that reaction between the by-product glycerine and the product zinc soap is substantially hindered, (iv) continuing said reaction to at least 95% completion, (v) allowing the reaction mixture to separate into an aqueous layer and a molten layer of zinc soap substantially free of zinc oxide, carboxylic acid and glyceryl ester, under a pressure such that said aqueous layer is essentially quiescent, and (vi) dissociating the molten zinc soap layer from the aqueous layer.

12. A process according to claim 11, wherein said temperature in (iii) is about 175° to 195° C., said reacting is carried out from 2 to 5 hours and said reaction mixture in (i) comprises water in an amount by weight of about 2 to about 7 times the stoichiometric amount by weight of glycerine produced according to equation (II).

13. A process according to claim 12, wherein step (v) includes introducing an inert gas to maintain a pressure above the reaction mixture above the vapour pressure of aqueous glycerine in the product reaction mixture, whereby boiling of the aqueous glycerine is prevented and said separate layers are formed.

14. A process according to claim 13, wherein said zinc oxide in said reaction mixture has a particle size not greater than 45 microns.

15. A process according to claim 13, wherein said agitating in (ii) is effective to disperse said triglyceride as small droplets having a size of 1 to 1,000 microns.

16. A process according to claim 15, wherein mono- and diglycerides are produced as intermediates in said reacting effective to maintain the small droplet size of triglycerides.

17. A process according to claim 14, wherein said triglyceride is hydrogenated tallow.

18. A process according to claim 14, wherein said triglyceride has an iodine value less than 10.

19. A process according to claim 13, wherein after step (iv) and prior to step (v) there is included a step of establishing a difference in density between the molten zinc soap and the aqueous glycerine, whereby the aqueous layer and the molten soap layer may form in step (v).

* * * * *